United States Patent [19]

Muck et al.

[11] Patent Number: 5,282,825
[45] Date of Patent: Feb. 1, 1994

[54] SURGICAL LIGATURING AND ANIMAL RESTRAINING DEVICE

[76] Inventors: Kin C. Muck; Helen M. Chan, both of 4437 Greenfield Rd., Bethlehem, Pa. 18017

[21] Appl. No.: 70,207

[22] Filed: Jun. 2, 1993

[51] Int. Cl.$^5$ .................... A61B 17/12; A01K 29/00
[52] U.S. Cl. ........................... 606/203; 24/115 H; 24/130; 119/804; 294/19.1
[58] Field of Search ............... 606/203, 113, 121, 122, 606/158, 157, 151; 24/115 H, 129 R, 130; 119/802, 803, 804; 294/19.1, 119.2

[56] References Cited

U.S. PATENT DOCUMENTS

| | | |
|---|---|---|
| 1,167,223 | 1/1916 | Sheidler . |
| 1,532,299 | 4/1925 | Braecklein . |
| 3,877,434 | 4/1975 | Ferguson et al. ............... 606/203 X |
| 3,910,280 | 10/1975 | Talonn ............... 24/130 X |

Primary Examiner—Michael H. Thaler

[57] ABSTRACT

A surgical ligaturing and restraining device for small animals comprises an elongated tubular body member (10) having a noose (28) at the front end (18) operable from the rear end (12) of the body. The body front end is fitted with a cap (20) with two holes (22) (24) through its face. The noose is formed by a flexible and elastic cable (26), one end (25) of the cable is looped around passing through the holes in the cap. Said cable end (25) is attached to the cable itself around cable middle portion by attachment means (30). The cable runs through the inside of the body and emerges substantially from the body rear end (12). The body rear end has two short longitudinally extending slots (14) (16), each slot has one extremity open to the rear end. The slots are diametrically opposite each other, dividing the tubular body into two sides (32) (34). One side (32) is made shorter than the opposite side (34), so as to facilitate the locking action. The device is applied by placing the noose around an object. The noose is tightened by pulling on the cable out of the body rear end. The tightened noose is locked by passing the cable through one of the slots, and wrapped around the body several times, before passing said cable through both slots, to complete the locking procedure.

11 Claims, 2 Drawing Sheets

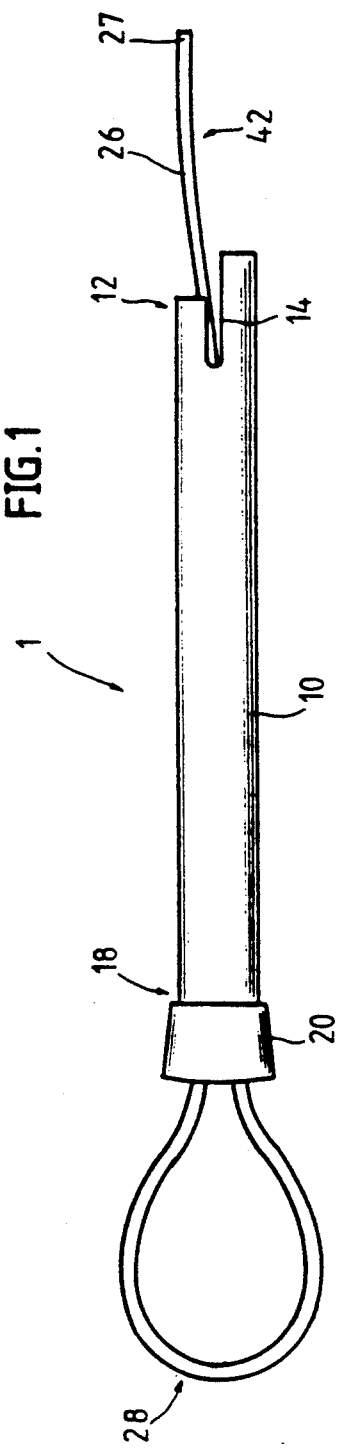
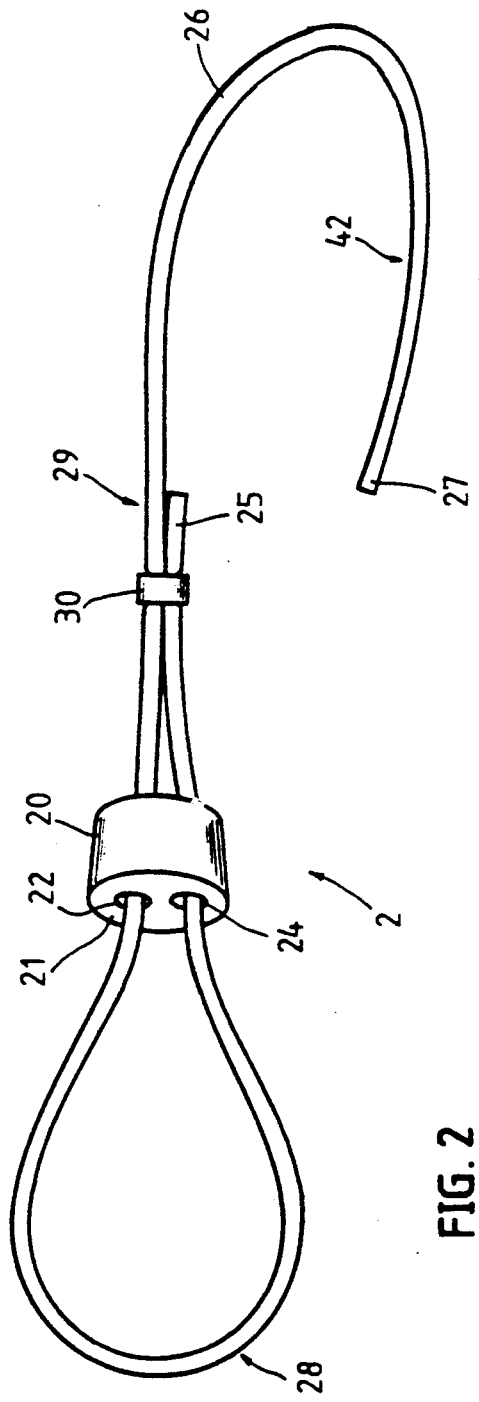

SURGICAL LIGATURING AND ANIMAL RESTRAINING DEVICE

BACKGROUND OF THE INVENTION

1. Technical Field

This invention relates in general to animal surgical ligaturing and restraining devices, and in particular to the kind characterized by an elongated tubular handle having at one end a noose operable from the other end of the handle. The invention is adapted for capturing and restraining small animals, and for restricting the flow of blood in the limbs as a tourniquet.

2. Description of Prior Art

In the field of medical and veterinary practice, it is often necessary to restrain the various members of an animal during treatment. Certain surgical procedures require the restriction of blood flow in the patient's limbs or legs. For these purposes, restraining devices such as snares and mouth muzzles, and ligaturing devices such as tourniquets are utilized.

Prior art restraining and ligaturing devices of the kinds similar to the present invention are generally comprised of a tubular body member having at the front end a noose which is operable from the rear end of the body. The noose is generally part of a flexible strap or cable, the cable running through the inside of the body, and extending out of the body's rear end. To apply, the noose is placed over and around the object, and is tightened by pulling on the cable extending out of the rear end of the body. To maintain the noose in its tightened state, various movable parts which are commonly located inside the body, are utilized to grip onto the cable tightly.

There is a wide variety of animal snares and restraining devices of the general class to which the present invention pertains. The snares are specifically designed to snare or capture an animal by the head. They are generally not suitable for use on the animal's jaw as a muzzle. The existing ligaturing devices such as tourniquets for stopping the flow of blood in the limbs are inadequate for use either as a muzzle or a snare. No known prior art device exist, which is versatile enough to be used for restraining the head or the mouth of an animal, and at the same time, effective as a tourniquet.

The devices described in U.S. Pat. No. 3,292,591 to F. A. Wood, U.S. Pat. No. 3,319,609 to G. C. Pickard et al, and U.S. Pat. No. 5,088,449 to L. Lamb Sr. et al, all have movable locking mechanisms located inside the body member. U.S. Pat. No. 1,167,223 to O. E. Sheidler describes a device which requires the attachment of the noose cable to a chain whose movable links are fitted into a slot in the tubular body as locking means. U.S. Pat. No. 2,488,962 to D. F. Christoffer describes a device which utilizes a studded rod inside the tubular body to lock the noose in place. These known prior art snares which are generally bulky and heavy, are ineffective for ligaturing purposes in stopping the flow of blood in the limb. The noose cables utilized are flexible but inelastic, and therefore cannot act as a tensioning ligature member.

The known prior art tourniquets of the present type described in U.S. Pat. No. 1,532,299 to A. H. Braecklein, U.S. Pat. No. 4,561,437 to H. Kirchner, and U.S. Pat. No. 5,084,062 to M. E. Sturm, generally comprise of a body member, at one end of the body is a looped flexible strap, the strap extends out of the other end of the body. Locking mechanisms located inside the body secure the noose in place after being tightened by pulling at the strap extending out of the body. These tourniquets are specifically designed for ligaturing a patient's limb, and are not suitable for restraining an animal, either by its head or its mouth. These known devices lack a substantial elongated handle which is an important requirement in the protection of a user's hand from the animal being restrained. Also the movable locking mechanisms inside the body are generally not strong enough to withstand the violent struggles of most restrained animals.

All these known prior art devices share a common feature. The locking means is comprised of movable parts which are separate and distinct from the noose strap and the body member. The obvious disadvantage of utilizing movable mechanical parts to lock the noose strap is that the parts can malfunction, thereby causing reliability problems. Additionally, the movable parts also add cost and weight to the manufacture. Therefore it is desirable to have a reliable and economical ligaturing and restraining device which requires no movable locking parts, other than the noose strap and the body member.

SUMMARY OF THE INVENTION

The invention is directed to an improved animal surgical ligaturing and restraining device which permits the omission of movable locking parts. The invention utilizes no separate locking mechanism other than a body member and a noose cable strap. The invention has the combined attributes of being very reliable, economical, lightweight, and easy to use. It is suitable for use not only as a tourniquet for ligaturing a patient's limb to stop the flow of blood, but also suitable for restraining the head or the mouth of a small animal.

The invention is generally comprised of an elongated tubular body member, a flexible and elastic cable strap, part of the cable forms a noose, and an end cap which has two separated holes through its face. The cap is fitted to the front end of the body, and is utilized as a stop for the noose. At the rear end of the body, there are two relatively short longitudinally extending slots. The length of each slot is several times its width. The slots are advantageously diametrically opposite each other. Each slot has one end opened to the body rear end. The total length of the cable is substantially longer than the body. The external diameter of the cable is slightly greater than the width of the slots. The cable runs through the inside of the hollow body, and a portion of it extends out of the body's slotted rear end. At the cap fitted front end, the cable emerges as a noose through the two holes in the cap. To prevent the noose from becoming undone, the cable is attached to itself by attachment means about its middle portion.

To apply the device, the noose is first enlarged by pulling away from the cap. The noose is placed over and around the object, and tightened by pulling on the cable at the slotted end of the body. The tightened loop is prevented from loosening by a wrapping method about the slotted end of the body in the manner which will be explained in a detailed description of the invention contained herein.

The two slots at the slotted end split the body into two sides. In one preferred embodiment, for the purpose of facilitating the wrapping-locking action, the body on one side of the diametrically opposite slots is made longer than the other side. The locking method utilized in the invention is extremely strong and reliable, with little likelihood of malfunction.

The present invention can be utilized as a lasso snare for restraining an animal's head, or as a mouth muzzle for biting animals. It is also used as a tourniquet for restricting blood flow to the limbs. When utilized as a muzzle or a tourniquet, the elongated body serves as a handle which is a unique and useful feature.

In another embodiment of the invention, the cap is omitted. The cable is attached to the body at its front end on one side. The cable is looped around to form a noose, and fed through the inside the body, until it emerges from the body's slotted rear end. The operation of this embodiment is similar to the one described above. However, by attaching the cable directly to the body, instead of attaching the cable to itself, the travel of the cable is about twice as much during tightening.

Accordingly, it is an object of the invention to provide a device for ligaturing a patient's arm or leg to stop the flow of blood during certain surgical procedures.

Another object of the invention is to provide a device useful for restraining the head of an animal in the form of a lasso snare, and also as a muzzle to restrain its mouth or jaw.

Yet another object of the invention is to provide a device which is versatile enough to be used as a tourniquet, as a lasso snare, and also as a mouth muzzle for an animal.

A further object of the invention is to provide a ligaturing and restraining device which has a very strong and reliable locking method.

A still further object of the invention is to provide a ligaturing and restraining device whose locking method does not require the utilization of any movable locking parts, other than the body member and the noose cable.

It is yet another object of the invention to provide a device which is simple in design, easy to use, highly efficient in operation, rugged in construction, lightweight, and also economical to manufacture.

BRIEF DESCRIPTION OF THE DRAWINGS

In the drawings, closely related figures have the same number but different alphabetic suffixes.

FIG. 1 shows an overall plan view of an animal surgical ligaturing and restraining device according to a preferred embodiment of the invention.

FIG. 2 shows a fragmentary perspective view of the invention, on an enlarged scale, of the noose and cap assembly.

DETAILED DESCRIPTION OF THE INVENTION

Figure 3:
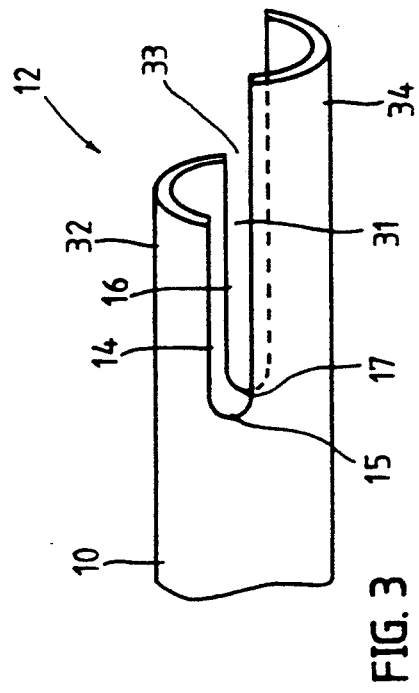
FIG. 3 is a fragmentary perspective view, on an enlarged scale, of the slotted rear end of the device.

A preferred embodiment of the invention is illustrated in its perspective views in FIG. 1 to FIG. 3.

In carrying out the present invention of an animal surgical ligaturing and restraining device 1, there is provided a tubular body member 10, as shown in FIG. 1. Said body 10 is preferably a length of PVC tubing. Said body 10 has a body rear end 12, and a body front end 18. Said body front end 18 is customarily truncated in a substantially flat fashion. An end cap 20 is fitted to said body front end 18. Said cap 20 is advantageously releasably attached to said body 10.

Referring to FIG. 1 and FIG. 2, said Cap 20 has a substantially flat cap face 21. There are two through holes 22, 24 on said cap face 21. Said holes 22, 24 are separated from each other. There is provided a flexible cable 26 which has first cable end 25, second cable end 27, and cable middle portion 29. Said cable 26 is substantially thinner than said body 10 internal diameter. Said cable 26 is proportionately about two and a half times the length of said body member 10. Said first cable end 25 is passed through said hole 22 from behind said cap face 21, and subsequently passed through said hole 24 from in front of said cap face 21, in order to form a noose 28. Said noose 28 is prevented from becoming undone by attaching said first cable end 25 to said cable middle portion 29 by attachment means 30. In the preferred embodiment, said attachment means 30 is a cable tie. Said cable 26 thus forms a noose-cable assembly 2 in which said noose 28 is on one side of said attachment means 30, and a cable tail 42 on the other side of said attachment means 30. In the preferred embodiment, said cable 26 is made of an elastic and flexible plastic tubing material, such as polyurethane. Other suitable materials such as rubber can also be used. In the preferred embodiment, the internal diameter of said tubular body 10 is greater than twice the external diameter of said cable 26. Said holes 22, 24 have internal diameters slightly larger than the external diameter of said cable 26, so as to allow said cable 26 to pass through easily. Said cable tail 42 is long enough to emerge substantially from said body 10 at said body rear end 12.

Referring to FIG. 1 and FIG. 3, said rear end 12 of said body 10 has two longitudinally extending slots 14, 16. Said slots 14, 16 are preferably diametrically opposite each other, and are of about the same length. Said slots 14, 16 are of length several times the external diameter of said cable 26. In the preferred embodiment, the widths of said slots 14, 16 are slightly smaller than the external diameter of said cable 26. Said slot 14 has two ends or extremities 15, 31. Said extremity 15 is closed, while said extremity 31 is opened to said body rear end 12, as depicted in FIG. 3. Similarly, said slot 16 has two extremities, 17, 33. Said extremity 17 is closed, while said extremity 33 is opened to said body rear end 12. Said body 10 at said rear end 12 is divided into two sides, namely, first rear side 32 and second rear side 34, by said diametrically opposite slots 14, 16. In the preferred embodiment, said first rear side 32 is shorter than said opposite second rear side 34 by about two times the external diameter of said cable 26. The purpose of making said rear sides 32, 34 of different lengths is to facilitate the locking operation of the device, as will be described herein.

Figure 4:
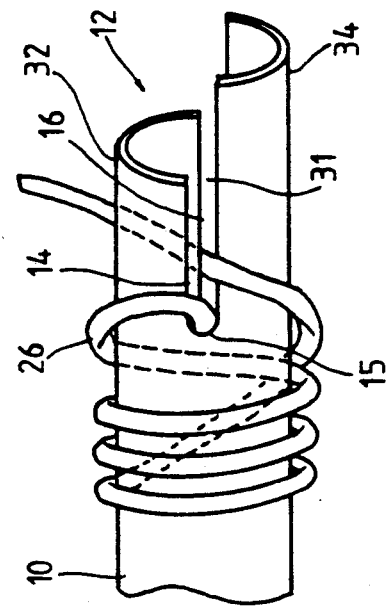
FIG. 4 shows a preferred method of locking the tightened noose by wrapping the cable strap about the slotted rear end of the device.

From the foregoing description, the mode of operation will be as follows:

Referring to FIG. 1, the noose 28 is first enlarged by pulling away from the cap 20. Said noose 28 is then placed over and around the object to be ligatured. Holding the device body member 10 with one hand, said noose 28 is tightened around the object by pulling on the cable tail 42. When suitably tight, the noose is prevented from becoming loose by locking said cable tail 42 about the slotted rear end portion 12 of said body member 10. Referring to FIG. 4, locking is achieved by first passing the cable 26 which emerges out of said body rear end 12, through slot 14 via its opened extremity 31, while exerting steady pulling tension all the time on said cable 26, until said cable 26 is stopped at the closed extremity 15 of said slot 14. Said cable 26 is then wrapped around said body 10 about said body rear end 12. It is preferred that said cable 26 be wrapped around said body 10 several times for a very strong lock. The wrapping of said cable 26 around said body 10 should leave said slot 14, and the opposite slot 16 substantially uncovered, as depicted in FIG. 4. After said cable 26 is wrapped round said body 10 several times, said cable 26 is fed through said slot 14 and said slot 16, in order to hold the wrapping in place. The presence of said slots 14, 16 split said body rear end 12 into first rear side 32 and second rear side 34. Said second rear side 34 is made longer than said first rear side 32 in order to facilitating the locking action of passing said cable 26 through said slot 14 and said slot 16 simultaneously. Frictional forces which naturally occur at all points of contact between said cable 26 and said body member 10 act to prevent the wrapping of said cable 26 from becoming undone. When thus secured, the object can be held in the ligatured or restrained position almost indefinitely without coming loose. The resulting lock is extremely strong; its strength is derived from the very large frictional forces exerted by the multiple wrapping of said cable 26 around body 10. The present locking method renders the invention unique from all known prior art devices of the present kind.

In general, making said slots 14, 16 narrower with respect to the external diameter of said cable 26 tends to increase the frictional forces which exist between said body 10 and said cable 26 as a result of the wrapping. It must be pointed out that similar frictional forces would still exist even if the widths of said slots 14, 16 are greater than the external diameter of said cable 26, as long as there are points of contact between said body 10 and said cable 26 due to the wrapping.

To release the restrained object from the device, said cable 26 is simply unwrapped until it is completely free from said slots 14, 16. Said noose 28 is then loosened by pulling away from said cap 20.

The combined attributes of the elongated body 10, the flexible and elastic noose-cable 26, and a very strong and rugged locking method renders the invention a very versatile tool suitable for use not only as a tourniquet, but also as a restraining device in the form of a mouth muzzle or a lasso snare.

In the preceding embodiment, the locations of said first cable end 25 and said attachment means 30 about said cable middle portion 29 of said cable 26 is merely a convenience. Said cable end 25 and said attachment means 30 can be placed at any location along said cable 26, as long as the resulting assembly provides a noose of sufficient size so as to render the device useful for various intended purposes. In fact, in forming the noose-cable assembly, said first cable end 25 can be placed adjacent to said second cable end 27, and said attachment means 30 can be located anywhere along said cable 26, provided of course that a noose of appropriate size is attained.

Figure 5:
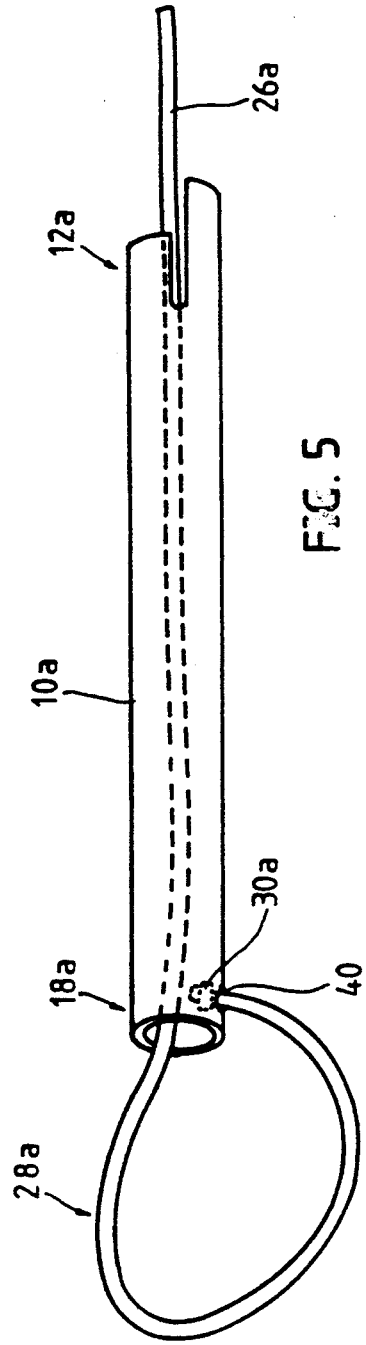
FIG. 5 shows a side elevation view of another embodiment of the invention which omits the utilization of an end cap as a stop for the front end of the device.

FIG. 5 shows another embodiment of the invention. In this embodiment, a tubular body member 10a also has a slotted body rear end 12a, and a body front end 18a which is customarily truncated in a substantially flat fashion. Said slotted rear end 12a is in every aspect similar to the slotted rear end 12 of the previously described embodiment shown in FIG. 1. A hole 40 is made on one side adjacent said front end 18a of said body 10a.

A flexible and elastic cable 26a is attached to said body 10a via said hole 40 by attachment means 30a. The internal diameter of said hole 40 is slightly larger than the external diameter of said cable 26a. Said cable 26a is looped around to form a noose 28a which protrudes out of said body front end 18a, and is passed through the inside of said body 10a, until said cable emerges from said body slotted rear end 12a. Said cable 26a being long enough to emerge substantially from said slotted body rear end 12a. Other than the manner in which said cable 26a is attached to said body 10a and said noose 28a is formed, without the utilization of a cap, the essential design and operation of this present embodiment is identical to that of the previously described embodiment.

RAMIFICATIONS AND SCOPES

Although the detailed description above contains many specificities, these should not be construed as limiting the scope of the invention. While two specific embodiments of the invention have been disclosed for the purpose of illustrating the principles of the invention, it is to be understood that the invention is not limited to these embodiments, and that various changes in its form, modifications in the design, proportions and minor details of construction, arrangement of parts, and instrumentalities of the invention are possible, and the right is herein reserved to make such changes as properly fall within the spirit and scope of the appended claims.

The end cap described in the detailed description is essentially utilized as a stop for the noose cable. Its inclusion is merely a matter of convenience. Other similar objects, such as a stopper, or a cover at the noose end of the body will also suffice, as long as they perform similar functions. In fact, the present device will still perform satisfactorily according to the intended functionality, even if the end cap is excluded. Therefore the scope of the present invention is not limited to the nature and the presence of the end cap as described herein.

What is claimed is:

1. A surgical ligaturing and restraining device for small animals comprising:

an elongated tubular body having a body front end and a body rear end, said body front end being truncated in a substantially flat fashion, said body rear end having plurality of longitudinal extending slots, each said slot having one extremity opened to said body rear end;

an end cap fitted to said body front end, said cap having a substantially flat face with two separate through holes;

an elastic cable substantially thinner and longer than said body, said cable having a first cable end, a second cable end, and a cable middle portion;

attachment means for attaching said first cable end to said cable middle portion;

wherein in the assembled state of the device, said cable running through the interior of said tubular body, said second cable end emerging substantially from said body rear end, said cable also emerging through said holes in said cap forming a noose of appropriate size, said noose being retained in its configuration by attaching said cable adjacent said first cable end to said cable itself adjacent said cable middle portion by said attachment means; whereby during application, said noose is placed around an object and tightened by pulling on said cable emerging from said body rear end, said noose is held in its tightened state by passing said cable through one said slot, and wrapped around said body several times adjacent said slots, before said cable is reinserted into at least two said slots, thereby completing the locking action.

2. A device according to claim 1, wherein said body rear end of said elongated tubular body member has two longitudinally extending slots, said slots being diametrically opposite each other.

3. A device according to claim 1, wherein said body rear end of said elongated tubular body member has two longitudinally extending slots, said slots being diametrically opposite each other, said slots dividing said body adjacent said body rear end into first and second rear sides, said first rear side and said second rear side being diametrically opposite each other, said first rear side is shorter than said second rear side.

4. A device according to claim 1, wherein said cable is made of an elastic and flexible polyurethane plastic material.

5. A device according to claim 1, wherein said cable is made of a flexible and elastic rubber material.

6. A surgical ligaturing and restraining device for small animals comprising:
    an elongated tubular body having a body front end and a body rear end, said body front end being truncated in a substantially flat fashion, said body rear end having a plurality of longitudinal extending slots, each said slot having one extremity opened to said body rear end;
    an end cap fitted to said body front end, said cap having a substantially flat face with two separate through holes;
    an elastic cable substantially thinner and longer than said body, said cable having a first cable end, a second cable end;
    attachment means for attaching said cable to itself in order to form a noose;
    wherein in the assembled state of the device, said cable running through the interior of said tubular body, said cable emerging through said holes in said cap forming a noose of appropriate size, said first and second cable ends also emerging substantially from said body rear end, said noose being retained in its configuration by attaching said cable to itself utilizing said attachment means;
    whereby during application, said noose is placed around an object and tightened by pulling on said cable emerging from said body rear end, said noose is held in its tightened state by passing said cable through one said slot, and wrapped around said body several times adjacent said slots, before said cable is reinserted into at least two said slots, thereby completing the locking action.

7. A surgical ligaturing and restraining device for small animals comprising:
    an elongated tubular body having a body front end and a body rear end, said body front end being truncated in a substantially flat fashion, said tubular body having a hole adjacent said body front end, said body rear end having a plurality of longitudinal extending slots, each said slot having one extremity open to said body rear end;
    and flexible cable substantially thinner and longer than said body, said cable having a first cable end, and a second cable end;
    attachment means for securing said first cable end to said body through said hole adjacent said body front end;
    wherein in the assembled state of the device, said cable runs through the interior of said body, said first cable end is looped around to form a noose, and is attached to said body through said hole by said attachment means, said second cable end emerges substantially from said body rear end;
    whereby during application, said noose is placed around an object and tightened by pulling on said cable emerging from said body rear end, said noose is held in its tightened state by passing said cable through one said slot, and is wrapped around said body several times adjacent said slots, before said cable is reinserted into at least two said slots, thereby completing the locking action.

8. A device according to claim 7, wherein said body rear end of said elongated tubular body member has two longitudinally extending slots, said slots being diametrically opposite each other.

9. A device according to claim 7, wherein said body rear end of said elongated tubular body member has two longitudinally extending slots, said slots being diametrically opposite each other, said slots dividing said body adjacent said body rear end into first and second rear sides, said first rear side and said second rear side being diametrically opposite each other, said first rear side is shorter than said second rear side.

10. A device according to claim 7, wherein said cable is made of an elastic and flexible polyurethane plastic material.

11. A device according to claim 7, wherein said cable is made of a flexible and elastic rubber material.

* * * * *